(12) United States Patent
Takeuchi et al.

(10) Patent No.: US 11,666,706 B2
(45) Date of Patent: Jun. 6, 2023

(54) SYRINGE BARREL AND PRE-FILLED SYRINGE

(71) Applicant: TERUMO KABUSHIKI KAISHA, Tokyo (JP)

(72) Inventors: Katsuyuki Takeuchi, Tokyo (JP); Eiji Yagishita, Shizuoka (JP); Nobukazu Akaike, Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 450 days.

(21) Appl. No.: 16/169,283

(22) Filed: Oct. 24, 2018

(65) Prior Publication Data

US 2019/0054240 A1     Feb. 21, 2019

Related U.S. Application Data

(63) Continuation of application No. PCT/JP2017/016389, filed on Apr. 25, 2017.

(30) Foreign Application Priority Data

Apr. 25, 2016  (JP) .............................. JP2016-086947

(51) Int. Cl.
*A61M 5/31* (2006.01)
*A61M 5/00* (2006.01)
(Continued)

(52) U.S. Cl.
CPC ........... *A61M 5/3129* (2013.01); *A61M 5/001* (2013.01); *A61M 5/002* (2013.01); *A61M 5/3202* (2013.01);
(Continued)

(58) Field of Classification Search
CPC .. A61M 2005/3126; A61M 2005/3131; A61M 5/3129; A61M 2205/19;
(Continued)

(56) References Cited

U.S. PATENT DOCUMENTS 7,677,419 B2 * 3/2010 DiGregorio ......... A61M 5/3129
222/386
8,105,294 B2 * 1/2012 Araki ...................... B29C 45/00
604/207
(Continued)

FOREIGN PATENT DOCUMENTS

CN     101968408 A     2/2011
CN     104162211 A    11/2014
(Continued)

OTHER PUBLICATIONS

Extended European Search Report dated Nov. 5, 2019 for corresponding European Patent Application No. 17789549.7.
(Continued)

*Primary Examiner* — Shefali D Patel
(74) *Attorney, Agent, or Firm* — Foley & Lardner LLP (57) ABSTRACT

A syringe barrel includes: a hollow body portion that is configured such that a gasket is slidably insertable therein. The syringe barrel is made of a resin that has a total light transmittance of 80% or more. A scale is disposed at an inner circumferential surface or an outer circumferential surface of the body portion, the scale being visible from an outside of the syringe barrel and being configured to indicate a liquid amount. The scale is formed by (i) a stepped structure having a step height in a range of 0.001 to 0.15 mm in a radial direction, and/or (ii) an embossment.

15 Claims, 11 Drawing Sheets

(51) Int. Cl.
  *A61M 5/32*   (2006.01)
  *A61M 5/34*   (2006.01)
  *B32B 25/08*  (2006.01)

(52) U.S. Cl.
  CPC ..... *A61M 5/345* (2013.01); *A61M 2005/3126* (2013.01); *A61M 2005/3131* (2013.01); *A61M 2205/0238* (2013.01); *B32B 25/08* (2013.01)

(58) Field of Classification Search
  CPC ............ A61M 2205/583; A61M 5/001; A61M 5/002; A61M 5/28; A61M 2005/3125; A61M 2205/0238; B32B 25/08
  See application file for complete search history.

(56) References Cited

U.S. PATENT DOCUMENTS

| | | |
|---|---|---|
| 9,155,839 B1 | 10/2015 | Willis et al. |
| 2002/0088131 A1 | 7/2002 | Baxa et al. |
| 2004/0054332 A1 | 3/2004 | Ferguson |
| 2008/0033367 A1 | 2/2008 | Haury et al. |
| 2008/0156831 A1 | 7/2008 | Nakayama et al. |
| 2008/0230961 A1 | 9/2008 | Moesli et al. |
| 2008/0262435 A1 | 10/2008 | Erickson et al. |
| 2011/0276005 A1 | 11/2011 | Hioki et al. |
| 2012/0123345 A1 | 5/2012 | Felts et al. |
| 2013/0168393 A1 | 7/2013 | Nakano et al. |
| 2014/0110289 A1 | 4/2014 | Geuder |
| 2017/0135900 A1 | 5/2017 | Yano et al. |

FOREIGN PATENT DOCUMENTS

| | | |
|---|---|---|
| EP | 2 216 061 A1 | 8/2010 |
| JP | 09-039042 A | 2/1997 |
| JP | 2004-229750 A | 8/2004 |
| JP | 2006-016053 A | 1/2006 |
| JP | 2008-272162 A | 11/2008 |
| JP | 2010-505668 A | 2/2010 |
| JP | 5325247 B2 | 10/2013 |
| JP | 2014-195516 A | 10/2014 |
| JP | 2015-073635 A | 4/2015 |
| WO | WO-2005-032619 A1 | 4/2005 |
| WO | WO-2009-057378 A1 | 5/2009 |
| WO | WO-2011/059823 A1 | 5/2011 |
| WO | WO-2016/002686 A1 | 1/2016 |

OTHER PUBLICATIONS

International Searching Authority, "International Search Report," issued in connection with International Patent Application No. PCT/JP2017/016416, dated Aug. 1, 2017.

International Searching Authority, "Written Opinion," issued in connection with International Patent Application No. PCT/JP2017/016416, dated Aug. 1, 2017.

"Prefilled syringes—Part 6: Plastic barrels for injectables"; International Standard—ISO 11040-6:2012(E); First Edition; Apr. 1, 2012.

Office Action dated Dec. 1, 2020 in related Chinese Patent Application No. 201780022140.0.

Office Action dated Dec. 2, 2020 in counterpart Chinese Patent Application No. 201780021837.6.

Notice of Allowance dated Feb. 10, 2021 for U.S. Appl. No. 16/169,392.

Extended European Search Report dated Jan. 30, 2020 in European Patent Application No. 17789538.0.

* cited by examiner

SYRINGE BARREL AND PRE-FILLED SYRINGE

CROSS-REFERENCE TO RELATED APPLICATIONS

The present application is a bypass continuation of PCT Application No. PCT/JP2017/016389, filed on Apr. 25, 2017, which claims priority to Japanese Appl. No. 2016-086947, filed on Apr. 25, 2016. The contents of these applications are hereby incorporated by reference in their entireties.

BACKGROUND

The present disclosure relates to a syringe barrel and a prefilled syringe.

Conventionally, for example, a prefilled syringe, which is one element of an injector, includes a barrel that enables a needle unit to be connected to a distal end portion thereof, a gasket slidably inserted in the barrel, and a drug solution filling a liquid chamber formed between the barrel and the gasket. In an initial state before use, the barrel is filled with a drug solution in an amount larger than a dose to a patient. Prior to administration to the patient, a user advances the gasket to a position of a scale disposed on an outer surface of the barrel in order to adjust the amount of the drug solution in the barrel to a predetermined dose while removing air inside the barrel.

As a method of attaching the scale to the barrel, there is a method of wrapping a label on a barrel as disclosed in JP 2008-272162 A. As another method of attaching the scale, there is a method of forming a concavo-convex shape on a barrel surface by molding as disclosed in JP 2014-195516 A.

SUMMARY

In the method of wrapping the label on the barrel as disclosed in JP 2008-272162 A, there is a problem that the accuracy of the scale is low. According to the method of forming the concavo-convex shape on the barrel surface by molding as disclosed in JP 2014-195516 A, it is possible to attach the scale with high accuracy. However, when a barrel is molded with a resin having high transparency such as a cyclic olefin polymer, there is a problem that visibility is poor because the scale is inconspicuous when formed using merely the concavo-convex shape.

Certain embodiments described in the present application have been developed in view of such problems, and one object thereof is to provide a syringe barrel and a prefilled syringe in which a barrel made of a resin having high transparency is provided with a scale with high visibility using a concavo-convex shape formed on a barrel surface.

According to one embodiment, a syringe barrel comprises a hollow body portion that is configured such that a gasket is slidably insertable therein. The syringe barrel is made of a resin having a total light transmittance of 80% or more in a measurement method according to ASTM-D1003, a scale, which is visible from an outside of the syringe barrel and indicates a liquid amount, is disposed on an inner circumferential surface or an outer circumferential surface of the body portion. The scale is formed by a stepped structure having a step height of in a range of 0.001 to 0.15 mm in a radial direction, or embossment.

According to the syringe barrel having the above configuration, the scale disposed on the inner circumferential surface or the outer circumferential surface of the body portion is configured using the stepped structure having a height in a predetermined range or the embossment. Such a stepped structure or embossment is conspicuous as the scale even when being disposed on the syringe barrel with high transparency. Therefore, the syringe barrel including the scale with high visibility is provided according to the present invention.

In the above syringe barrel, the stepped structure may be disposed on the inner circumferential surface.

With this configuration, it is difficult for the gasket and a position of the scale when viewed from the outside of the syringe barrel to visually deviate from each other, and it is possible to easily align the gasket to the position of the scale.

In the syringe barrel, the scale may be formed in an annular shape extending in a circumferential direction of the body portion.

With this configuration, the stepped structure continues circumferentially one round, and thus, it is possible to improve the visibility as the scale.

In the above syringe barrel, the scale includes a plurality of scale portions located at intervals in the circumferential direction of the body portion.

Even if the scale has a circumferentially discontinuous configuration in this manner, the function as the scale can be sufficiently exhibited.

In the above syringe barrel, the stepped structure may comprise a protrusion protruding radially from the inner circumferential surface or the outer circumferential surface.

With this configuration, the stepped structure functioning as the scale can be provided with a simple structure.

In the above syringe barrel, the stepped structure may comprise a groove recessed radially with respect to the inner circumferential surface or the outer circumferential surface.

With this configuration, the stepped structure functioning as the scale can be provided with a simple structure.

In the above syringe barrel, the inner circumferential surface or the outer circumferential surface may comprise: a large-diameter portion extending in an axial direction and a small-diameter portion extending in the axial direction and including a smaller diameter than the large-diameter portion, and the stepped structure may be formed by a change in diameter between the large-diameter portion and the small-diameter portion.

In this manner, it is possible to easily construct the stepped structure by providing a difference in diameter on the circumferential surface.

In the above syringe barrel, an axial width of the scale may be set to be 0.1 to 0.5 mm.

With this configuration, it is possible to obtain good visibility as the scale and to suppress a variation in a liquid amount of the drug solution when the gasket is aligned to the scale.

In the above syringe barrel, the stepped structure may comprise a protrusion that protrudes radially from the inner circumferential surface of the body portion, and the embossment may be formed on an inner circumferential surface of the protrusion.

With this configuration, it is possible to improve visibility of the scale.

In the above syringe barrel, the scale may be formed on the inner circumferential surface of the body portion and is formed using the embossment, the inner circumferential surface of the body portion may comprise a substantially constant inner diameter in an axial range in which the gasket slides in the body portion when using a prefilled syringe including a drug solution that is filled in a liquid chamber formed by the syringe barrel and the gasket.

With this configuration, there is substantially no step in a sliding range of the gasket at the time of use, and thus, it is possible to suppress an increase in a sliding resistance of the gasket and to suppress a decrease in liquid tightness when the gasket passes through the scale.

According to another embodiment, a prefilled syringe includes: any one of the syringe barrels described above; a gasket slidably inserted inside the syringe barrel; a plunger that is configured to press the gasket in a distal end direction; and a drug solution that is filled in a liquid chamber formed by the syringe barrel and the gasket.

According to certain embodiments of the syringe barrel and prefilled syringe described in the present disclosure, a high-visibility scale can be disposed on the barrel surface in the barrel made of resin with high transparency.

DETAILED DESCRIPTION

Hereinafter, embodiments of a syringe barrel and a prefilled syringe will be described with reference to the accompanying drawings.

Figure 1:
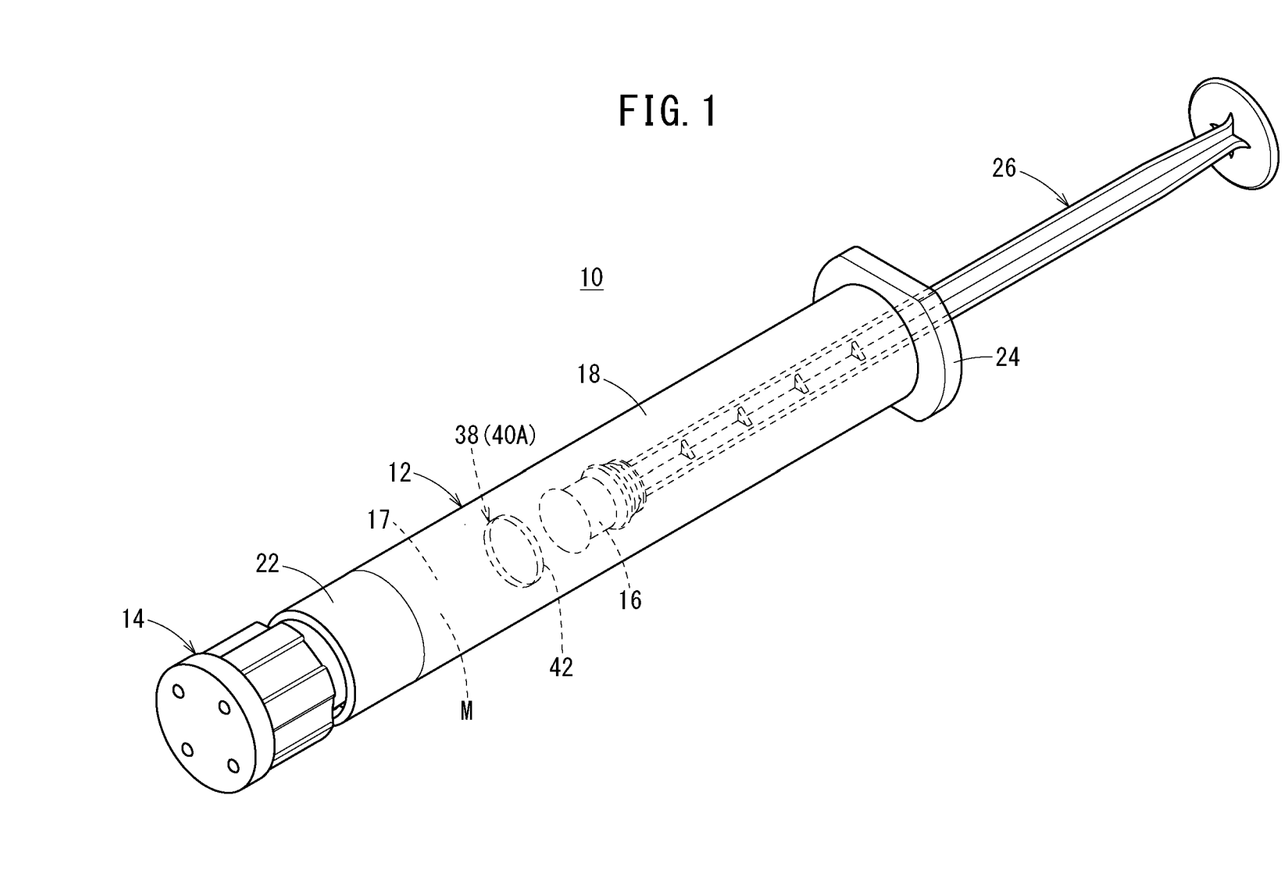
FIG. 1 is a perspective view of a prefilled syringe according to an embodiment of the present invention.
Figure 2:
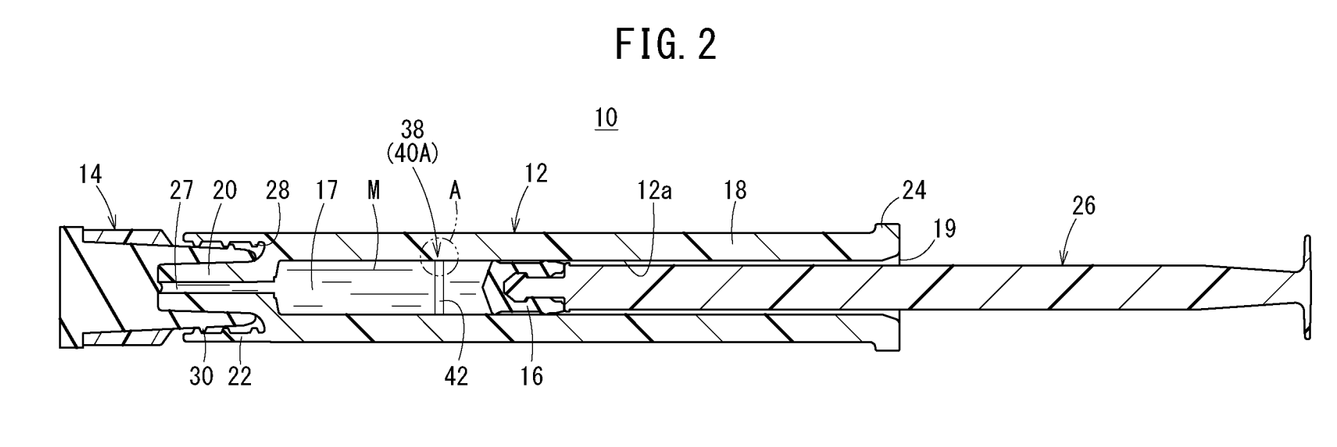
FIG. 2 is a cross-sectional view of the prefilled syringe according to the embodiment of the present invention.

A prefilled syringe 10 according to the present embodiment illustrated in FIGS. 1 and 2 includes, as main components, a syringe barrel 12 made of a hollow body provided with a tubular distal portion 20; a cap 14 sealing the tubular distal portion 20 of the barrel 12, a gasket 16 slidably inserted inside the barrel 12, and a drug solution M filling a liquid chamber 17 formed by the barrel 12 and the gasket 16. Hereinafter, the syringe barrel 12 will be simply referred to as the "barrel 12".

In FIG. 2, the barrel 12 includes: a body portion 18 having a substantially cylindrical shape and having a proximal-end opening portion 19 formed at a proximal end thereof, the tubular distal portion 20 disposed at a distal end of the body portion 18, a lock adapter 22 provided outside the tubular distal portion 20, and a flange 24 formed to protrude radially outward from the proximal end of the body portion 18.

In the illustrated barrel 12, the body portion 18, the tubular distal portion 20, the lock adapter 22, and the flange 24 are integrally molded. The barrel 12 can be manufactured, for example, by injection-molding.

The gasket 16 is inserted into the barrel 12 through a proximal end opening portion 19. The proximal end side of the barrel 12 is sealed by the gasket 16 in a liquid-tight manner, and the drug solution M is sealed in the barrel 12.

The gasket 16 is made of an elastic material such as a rubber material. An outer circumferential portion of the gasket 16 is in liquid-tight contact with an inner circumferential surface 12a of the barrel 12 and is arranged to be slidable inside the barrel 12. A distal end portion of the plunger 26 is connected to the gasket 16. As the user presses the plunger 26 in a distal end direction, the gasket 16 slides in the distal end direction inside the barrel 12. Incidentally, the plunger 26 may be connected to the gasket 16 at the time of administering the drug solution M to a patient. In addition, the plunger 26 is preferably capable of pressing the gasket 16 in the distal end direction, and may be configured to simply abut the gasket 16 without being connected to the gasket 16.

As illustrated in FIG. 2, the tubular distal portion 20 is reduced in diameter from the center of the distal end of the body portion 18 with respect to the barrel 12 and extends in the distal end direction. As illustrated in FIG. 2, the tubular distal portion 20 has a liquid passage 27 communicating with the liquid chamber 17 in the barrel 12 and passing through the tubular distal portion 20 in the axial direction.

A needle unit (not illustrated) can be attached to and detached from the tubular distal portion 20 in a state in which the cap 14 is detached from the tubular distal portion 20. The needle unit includes a needle body having a needle tip and a needle hub having a protrusion fixed to a proximal end portion of the needle body and protruding outward. The tubular distal portion 20 can be tapered to be fit to an inner circumferential portion of the needle hub. At the time of use of the prefilled syringe 10, the cap 14 is unplugged (removed from the tubular distal portion 20 and the lock adapter 22), and the needle hub of the needle unit is connected to the tubular distal portion 20 and the lock adapter 22 instead.

The lock adapter 22 illustrated in this example is configured in a substantially hollow cylindrical shape that extends in the distal end direction from the distal end of the body portion 18 and surrounds the tubular distal portion 20. A female screw portion 28 is formed on an inner circumferential surface of the lock adapter 22. The female screw portion 28 is detachably screwed with a male screw portion 30 disposed on the cap 14 in a mounted state of the cap 14. The female screw portion 28 can be engaged with the protrusion disposed on the needle hub of the needle unit described above in a state in which the cap 14 is detached from the barrel 12.

The lock adapter 22 illustrated in this example may be integrally formed at a proximal end portion of the tubular distal portion 20. Alternatively, the lock adapter 22 may be a member that is configured as a separate part from the body portion 18 and the tubular distal portion 20 and fixed to the barrel 12 or the tubular distal portion 20.

The barrel 12 is made of a resin having a total light transmittance of 80% or more in the measurement method according to ASTM-D 1003. As a result, the barrel 12 has high transparency, and the visibility of the drug solution M filling the liquid chamber 17 can be sufficiently secured. Examples of such a resin include a cyclic olefin polymer, a cyclic olefin copolymer, polycarbonate, and the like. Incidentally, the barrel 12 is preferably made of a resin having a total light transmittance of 90% or more in the measurement method according to ASTM-D 1003 in order to make the drug solution M filling the liquid chamber 17 easily visible.

In addition, a thickness of a side wall of the body portion 18 of the barrel 12 is preferably in a range of 1.5 to 2.5 mm. As a result, it is possible to suppress the sink mark at the time of injection-molding of the barrel 12 and to suppress the gas permeability at the side wall of the body portion 18 to be low. Because the gas permeability at the side wall of the body portion 18 is suppressed to be low, moisture evaporation from the drug solution M filling the liquid chamber 17 is suppressed, and it is possible to prevent the sterilizing gas from passing through the side wall of the body portion 18 and affecting the drug solution M when sterilizing the outer surface of the prefilled syringe 10 filled with the drug solution M with the sterilizing gas such as a hydrogen peroxide or ethylene oxide gas.

The cap 14 is detachably attached to the tubular distal portion 20, and seals a distal end opening portion of the tubular distal portion 20. The cap 14 in this illustrated example is configured to be attachable to and detachable from the tubular distal portion 20. The cap 14 is in liquid-tight contact with a distal end surface of the tubular distal portion 20 in a state in which the cap 14 is mounted to the tubular distal portion 20. As a result, the drug solution M does not leak out of the cap 14.

As illustrated in FIG. 2, a scale 38 that is visible from the outside of the barrel 12 is disposed on the inner circumferential surface 12a of the barrel 12 (the body portion 18). The scale 38 is used as a mark at the time of aligning the gasket 16 so as to adjust the amount of the drug solution M in the barrel 12 to a desired dose for a patient by advancing the gasket 16.

Figure 3:
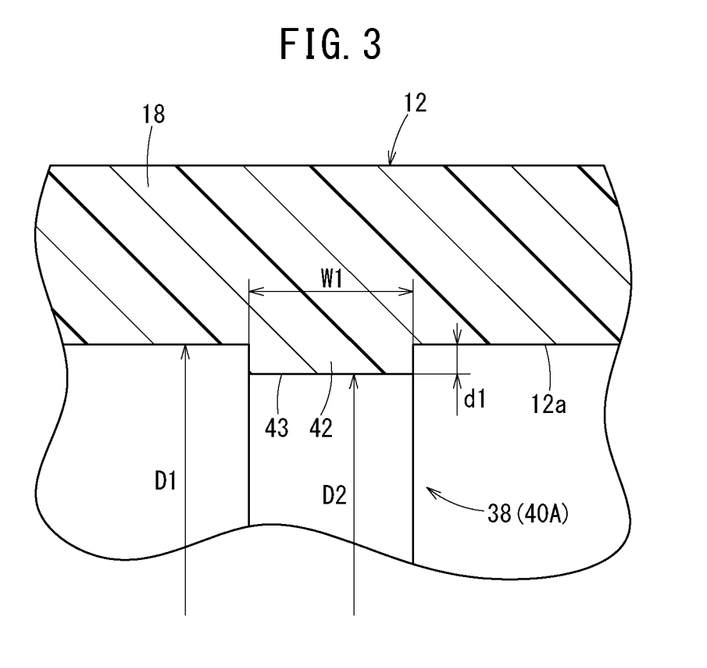
FIG. 3 is an enlarged view of a section A in FIG. 2.

Specifically, the scale 38 is formed using a stepped structure 40A disposed on the inner circumferential surface 12a of the barrel 12 (the body portion 18) in the present embodiment. As illustrated in FIG. 3, the stepped structure 40A has an annular protrusion 42 that protrudes radially inward from the inner circumferential surface 12a of the barrel 12. Because the way of refraction of light in an edge portion of the protrusion 42 forming the stepped structure 40A differs from the other parts, the portion of the protrusion 42 appears as a line along the circumferential direction of the barrel 12 when the barrel 12 having transparency is viewed from the outside. Therefore, the protrusion 42 functions as the scale.

In the prefilled syringe 10 in the initial state illustrated in FIG. 2, the barrel 12 is filled with the drug solution M in an amount larger than a dose to the patient. Therefore, the distal end portion of the gasket 16 is positioned closer to the proximal end side than the protrusion 42 forming the stepped structure 40A in the prefilled syringe 10 in the initial state. As illustrated in FIG. 3, an inner circumferential surface 43 of the protrusion 42 is parallel to the axial direction of the barrel 12. The inner circumferential surface 43 of the protrusion 42 may be inclined with respect to the axial direction of the barrel 12.

An inner diameter D2 of the protrusion 42 is smaller than an inner diameter D1 of the inner circumferential surface 12a of the portion where the protrusion 42 is not provided (the inner circumferential surface 12a axially adjacent to the protrusion 42). Therefore, a step height d1 (protrusion height of the protrusion 42) of the stepped structure 40A is (D1−D2)/2. In the barrel 12, the step height d1 is set to be 0.001 to 0.15 mm. When the step height d1 is 0.001 mm or more, good visibility as the scale 38 can be obtained. In addition, as the step height d1 is 0.15 mm or less, it is possible to suppress a sliding resistance of the gasket 16 from increasing in the process of advancing the gasket 16 inside the barrel 12, and further, it is possible to sufficiently secure liquid tightness when the gasket 16 moves over the protrusion 42. The step height d1 is preferably set to be 0.01 to 0.1 mm, and more preferably set to be 0.01 to 0.03 mm.

In addition, an axial width W1 of the protrusion 42, that is, an axial width of the scale 38 is set to be 0.1 to 0.5 mm. As the axial width of the scale 38 is 0.1 mm or more, good visibility of the scale 38 can be obtained. In addition, because the axial width of the scale 38 is 0.5 mm or less, it is possible to suppress a variation in the liquid amount of the drug solution M when the gasket is aligned with the scale 38. The axial width of the scale 38 is preferably set to be 0.2 to 0.4 mm.

Next, operations and effects of the syringe barrel 12 and the prefilled syringe 10 configured as described above will be described.

At the time of use of the prefilled syringe 10, a user such as a doctor or a nurse first removes the cap 14 from the barrel 12 to expose the tubular distal portion 20, and mounts the above-described needle unit to the tubular distal portion 20.

Next, the user advances the gasket 16 so as to adjust the amount of the drug solution M in the barrel 12 to the desired dose to the patient while removing air inside the barrel 12. Specifically, the user presses the plunger 26 in the distal end direction to advance the gasket 16 connected to the distal end of the plunger 26. As the gasket 16 advances, the drug solution M is discharged from the distal end opening portion of the tubular distal portion 20.

In this case, the scale 38, formed using the stepped structure 40A having the protrusion 42, is disposed on the inner circumferential surface 12a of the barrel 12. Therefore, it is possible to adjust the amount of the drug solution M in the barrel 12 to a desired dose by advancing the gasket 16 such that the position of the distal end portion of the gasket 16 is aligned to the position of the scale 38 (the protrusion 42).

Next, the user punctures the patient with the needle body of the needle unit connected to the barrel 12, and moves the plunger 26 in the distal end direction to administer the drug solution M into a body of the patient.

As described above, the scale 38 disposed on the inner circumferential surface 12a of the barrel 12 is formed using the stepped structure 40A having a height in a predetermined range in the barrel 12 of the prefilled syringe 10 according to the present embodiment. The above stepped structure 40A is conspicuous as the scale 38 even when being provided in the barrel 12 made of highly transparent resin. Therefore, the barrel 12 including the high-visibility scale 38 is provided. In addition, because only the single scale 38 is provided in the axial direction of the barrel 12, the scale 38 is more likely to be conspicuous.

In the present embodiment, because the stepped structure 40A is disposed on the inner circumferential surface 12a of the barrel 12, it is difficult for the gasket 16 and the position of the scale 38 to visually deviate from each other when viewed from the outside of the barrel 12, and it is possible to easily align the gasket 16 to the position of the scale 38.

In the present embodiment, the stepped structure 40A has the protrusion 42 that protrudes radially inward from the inner circumferential surface 12a of the barrel 12. With this configuration, the stepped structure 40A functioning as the scale can be provided with a simple structure.

In the present embodiment, the protrusion 42 forming the stepped structure 40A is formed in an annular shape extending in the circumferential direction of the barrel 12. With this configuration, the stepped structure 40A continues circumferentially one round, and thus, it is possible to improve the visibility of the scale.

The concavo-convex shape to provide the scale 38 visible from the outside of the barrel 12 is not limited to the stepped structure 40A having the protrusion 42 protruding from the inner circumferential surface 12a of the body portion 18. Therefore, configurations illustrated in FIG. 4 to FIG. 11 may be adopted in the barrel 12 instead of the stepped structure 40A described above.

Figure 4:
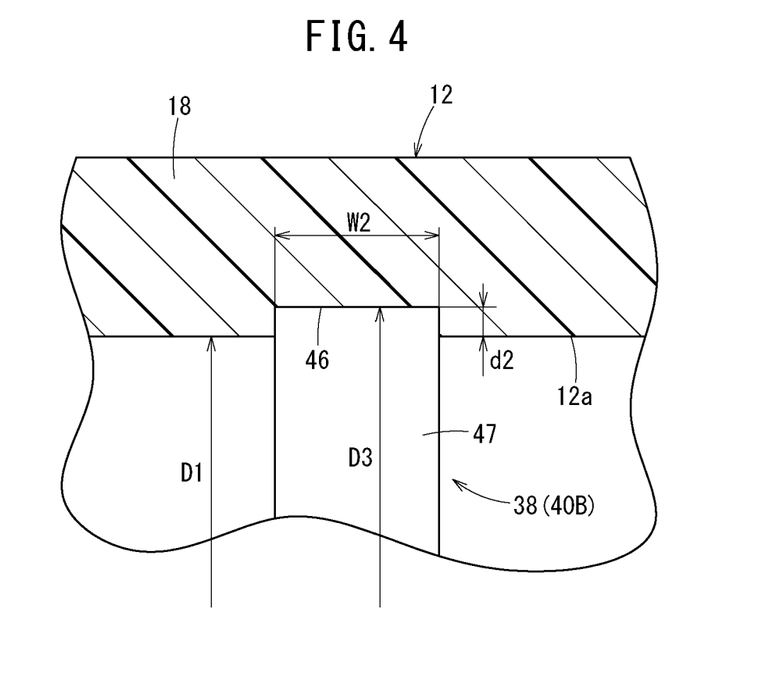
FIG. 4 is an enlarged cross-sectional view of a main part of a syringe barrel having a stepped structure according to a second configuration example.

A stepped structure 40B illustrated in FIG. 4 has an annular groove 46 recessed radially outward with respect to the inner circumferential surface 12a of the barrel 12. Therefore, an inner diameter D3 of the groove 46 is larger than the inner diameter D1 of the inner circumferential surface 12a of the portion where the groove 46 is not provided. An inner circumferential surface 47 (a surface forming a bottom of the groove 46) of the groove 46 in the illustrated example is parallel to the axial direction of the barrel 12. An inner circumferential surface 47 of the groove 46 may be inclined with respect to the axial direction of the barrel 12. A range of a step height d2 (a depth of the groove 46) of the stepped structure 40B is the same as a range of the step height d1 of the stepped structure 40A described above. A range of an axial width W2 of the groove 46 may be the same as a range of the axial width W1 (see FIG. 3) of the protrusion 42 described above.

Even with the above stepped structure 40B, the scale 38 with high visibility can be provided with a simple configuration. In addition, the stepped structure 40B can also provide the same operations and effects as those of the stepped structure 40A described above.

Figure 5A:
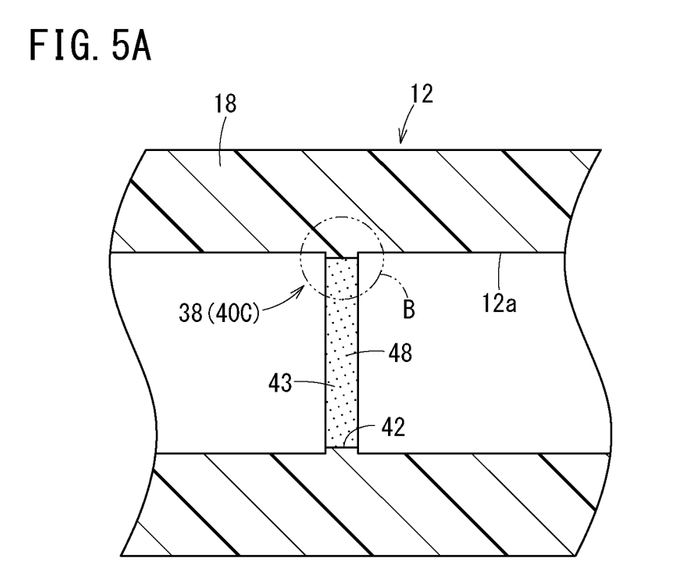
FIG. 5A is a partially omitted cross-sectional view of a syringe barrel having a stepped structure according to a third configuration example.
Figure 5B:
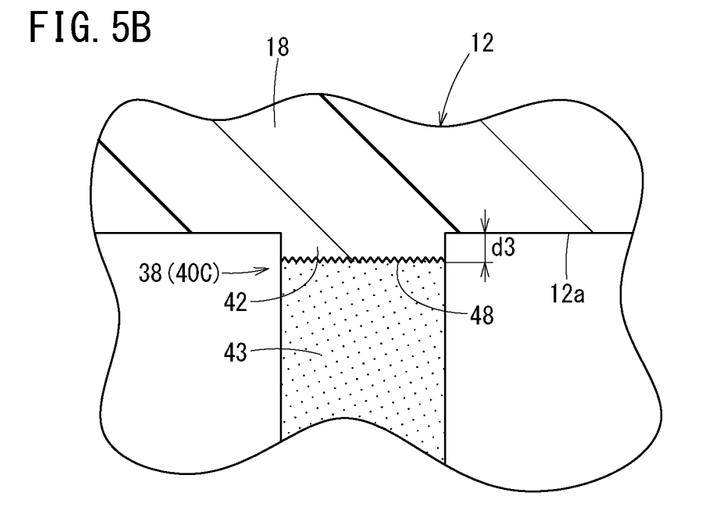
FIG. 5B is an enlarged view of a portion B in FIG. 5A.

The scale 38 illustrated in FIGS. 5A and 5B is formed by a stepped structure 40C having embossment 48. In this stepped structure 40C, the embossment 48 (a rough surface due to fine irregularities) is formed on the inner circumferential surface 43 of the protrusion 42 in the stepped structure 40A described above. A range of a step height d3 of the stepped structure 40C (a height of the protrusion 42 on which the embossment 48 is formed) is the same as the range of the step height d1 (see FIG. 3) of the stepped structure 40A described above. The embossment 48 is formed in an annular shape extending around the entire circumference of the inner circumferential surface 43 of the protrusion 42. In addition, the embossment 48 may be formed at a plurality of locations at intervals in the circumferential direction on the inner circumferential surface 43 of the protrusion 42.

When the barrel 12 is formed by injection-molding, fine irregularities corresponding to the embossment 48 are formed on a surface of a core pin forming an inner mold of an injection-molding die, and such a core pin is used to perform the injection-molding of the barrel 12 so that it is possible to mold the barrel 12 with the embossment 48 on the inner circumferential surface. Examples of a method of providing the fine irregularities on the surface of the core pin may include chemical treatment by etching, sand blasting, polishing treatment, and the like. Incidentally, the core pin surface is exposed at the time of processing, the fine irregularities are easily formed thereon. In addition, the fine irregularities on the surface of the core pin do not interfere with an outer circumferential surface of the barrel 12 during the injection-molding of the barrel 12, and thus, the barrel 12 does not remain in an outer mold for injection-molding, that is, does not cause so-called cavity remnants.

According to the above stepped structure 40C, a difference in light transmittance between the body portion 18 of a part where the embossment 48 is provided and the body portion 18 of a part where the embossment 48 is not provided becomes large, and thus, it is possible to improve the visibility of the scale 38. In addition, the stepped structure 40C can also provide the same operations and effects as those of the stepped structure 40A described above.

Figure 6:
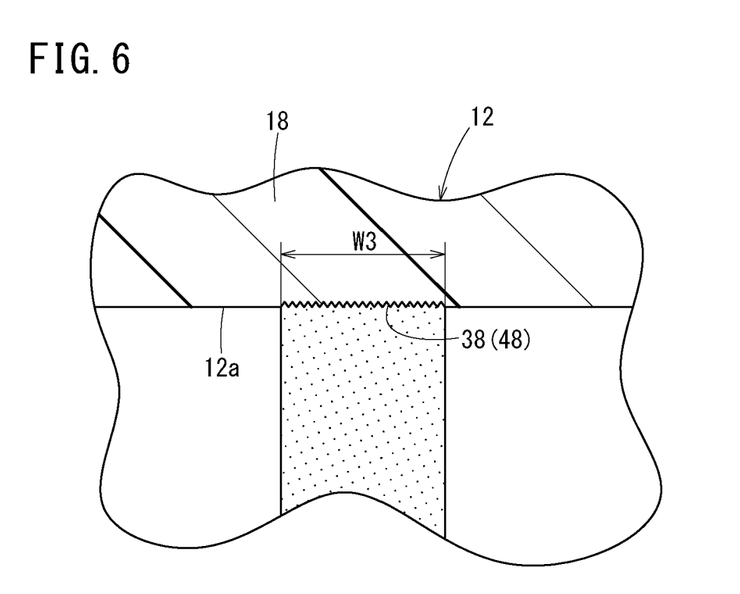
FIG. 6 is a partially omitted cross-sectional view of a syringe barrel having a scale formed using embossment.

In FIG. 5B, the protrusion 42 may be eliminated and the embossment 48 may be formed substantially without a step on the inner circumferential surface 12a of the barrel 12. That is, the scale 38 may be formed only by the embossment 48 as illustrated in FIG. 6. The inner circumferential surface 12a of the barrel 12 has substantially the same inner diameter in an axial range in which the gasket 16 slides inside the body portion 18 when using the prefilled syringe 10 in which the liquid chamber 17 formed by the barrel 12 and the gasket 16 is filled with the drug solution M. A range of an axial width W3 of the embossment 48 may be the same as the range (see FIG. 3) of the axial width W1 of the protrusion 42 described above.

Even with the configuration of FIG. 6, the scale 38 with high visibility is obtained. In addition, there is substantially no step in a sliding range of the gasket 16 at the time of use, and thus, it is possible to suppress an increase in a sliding resistance of the gasket 16 and to suppress a decrease in liquid tightness when the gasket 16 passes through the scale 38.

Figure 7A:
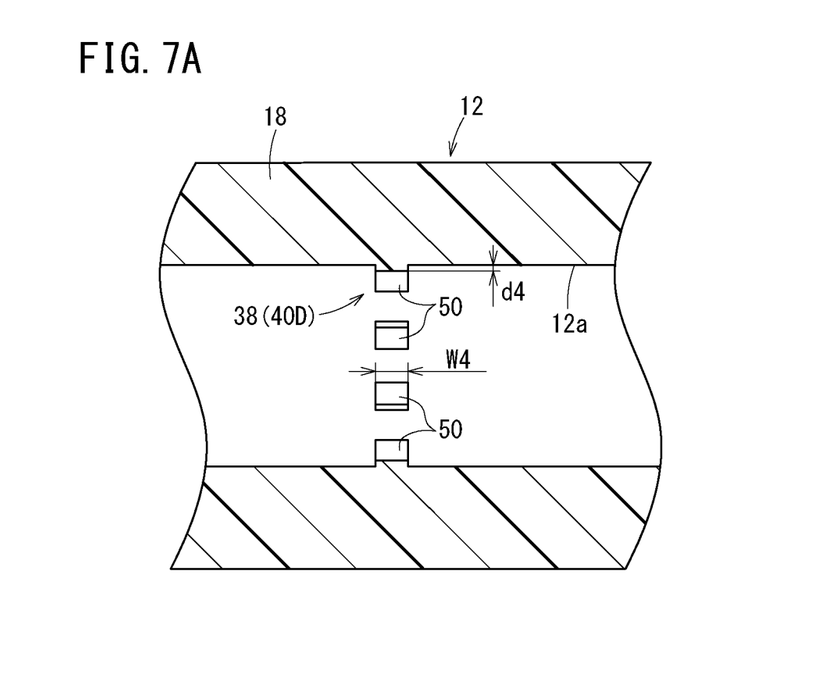
FIG. 7A is a partially omitted cross-sectional view of a syringe barrel having a stepped structure according to a fourth configuration example.

The stepped structure 40D forming the scale 38 illustrated in FIG. 7A includes a plurality of protrusions 50 provided at the inner circumferential surface 12a of the barrel 12 at intervals in the circumferential direction. A range of the step height d4 (a height of the protrusion 50) of the stepped structure 40D is the same as the range of the step height d1 (see FIG. 3) of the stepped structure 40A described above. A range of the axial width W4 of the protrusion 50 may be the same as the range of the axial width W1 (see FIG. 3) of the protrusion 42 described above. Even if the stepped structure 40D has a circumferentially discontinuous configuration in this manner, the function as the scale 38 can be sufficiently exhibited. Incidentally, a plurality of grooves may be disposed at intervals in the circumferential direction at the inner circumferential surface 12a of the barrel 12 instead of the plurality of protrusions 50.

Figure 7B:
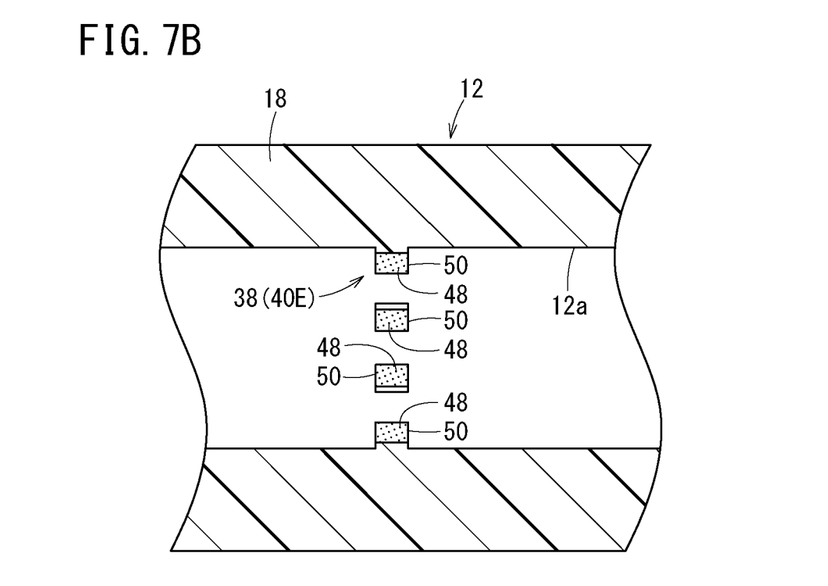
FIG. 7B is a partially omitted cross-sectional view of a syringe barrel having a stepped structure according to a fifth configuration example.

A stepped structure 40E forming the scale 38 illustrated in FIG. 7B is obtained by adding embossment 48 to each of inner surfaces of the plurality of protrusions 50 in the stepped structure 40D illustrated in FIG. 7A. By adding the embossment 48 as described above, it is possible to improve the visibility as a scale.

Figure 8:
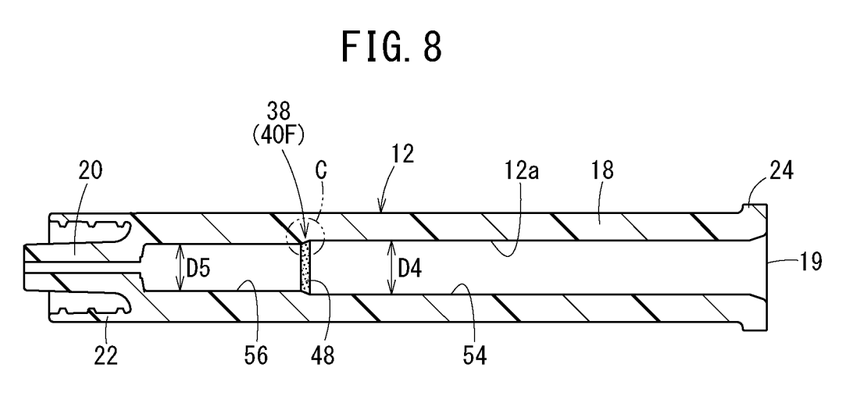
FIG. 8 is a cross-sectional view of a syringe barrel having a stepped structure according to a sixth configuration example.

A stepped structure 40F forming the scale 38 illustrated in FIG. 8 is formed using an inner diameter difference of the barrel 12. Specifically, the inner circumferential surface 12a of the barrel 12 has a large-diameter portion 54 extending in the axial direction and a small-diameter portion 56 extending in the axial direction and having a smaller inner diameter than the large-diameter portion 54. In FIG. 7, the small-diameter portion 56 is formed to be closer to the distal end side than the large-diameter portion 54.

Figure 9A:
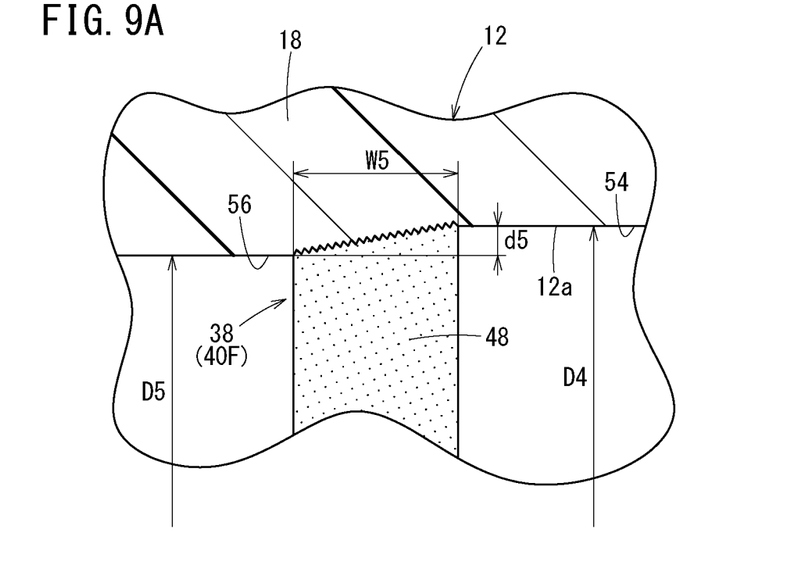
FIG. 9A is an enlarged cross-sectional view of a section C in FIG. 8.
Figure 9B:
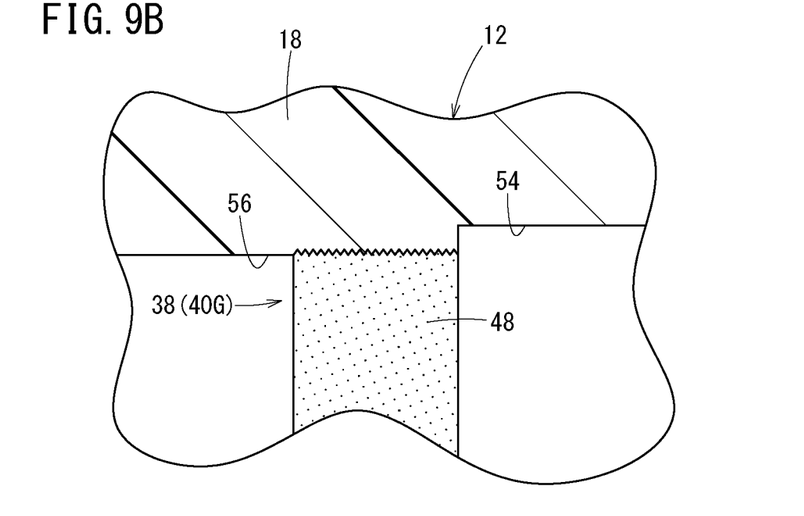
FIG. 9B is an enlarged cross-sectional view of a main part of a syringe barrel having a stepped structure according to a seventh configuration example.

As illustrated in FIG. 9A, a stepped structure 40F is configured using a difference in inner diameter between the large-diameter portion 54 and the small-diameter portion 56. A step height d5 of the stepped structure 40F is a half of a difference between an inner diameter D4 of the large diameter portion 54 and an inner diameter D5 of the small diameter portion 56. A range of the step height d5 of the stepped structure 40F is the same as the range of the step height d1 (see FIG. 3) of the stepped structure 40A described above.

In FIG. 9A, the embossment 48 is formed on an inner circumferential surface of a proximal end portion of the small-diameter portion 56. The embossment 48 is formed in an annular shape extending around the entire circumference in the circumferential direction. A range of an axial width W5 of the embossment 48 may be the same as the range of the axial width W1 (see FIG. 3) of the protrusion 42 described above. In this manner, the stepped structure 40F functioning as the scale 38 can be easily constructed by providing the inner diameter difference on the inner circumferential surface 12a of the barrel 12 and adding the embossment 48.

In addition, the inner circumferential surface of the proximal end portion of the small-diameter portion 56 is formed in a tapered shape increasing in diameter toward the proximal end direction, and the embossment 48 is formed on such a tapered inner circumferential surface. With this configuration, it is possible to suitably maintain the liquid tightness and the slidability of the gasket 16 when the gasket 16 moves from the large-diameter portion 54 to the small-diameter portion 56 in the process of advancing the gasket 16 (see FIG. 2) while improving the visibility of the scale 38.

The embossment 48 may be formed at a plurality of locations at intervals in the circumferential direction. The small-diameter portion 56 may be formed on the proximal end side of the large-diameter portion 54. Similar to a stepped structure 40G forming the scale 38 illustrated in FIG. 9B, the inner circumferential surface of the proximal end portion of the small-diameter portion 56 may be formed in a straight shape having an approximately constant inner diameter in the axial direction.

Figure 10A:
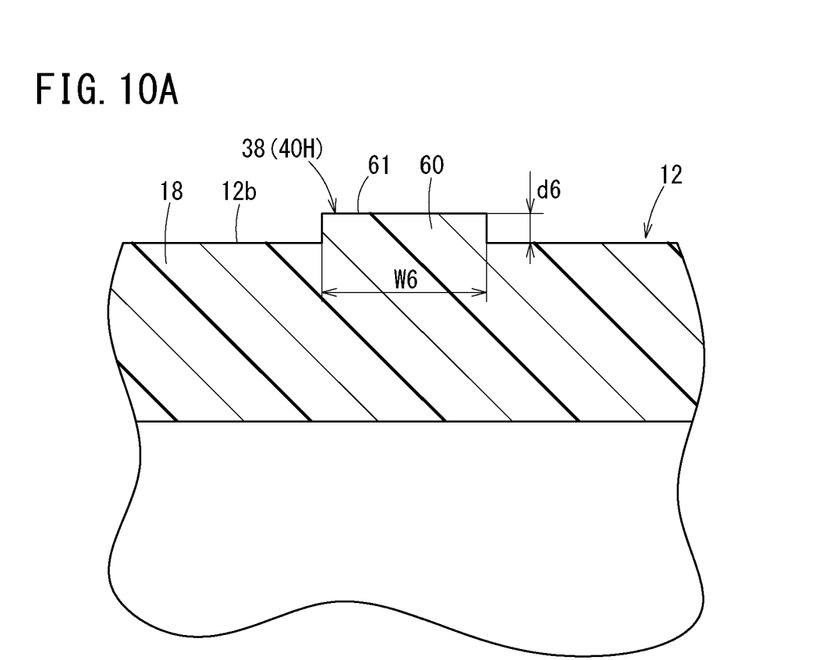
FIG. 10A is an enlarged cross-sectional view of a main part of a syringe barrel having a stepped structure according to an eighth configuration example.

A stepped structure 40H forming the scale 38 illustrated in FIG. 10A is disposed at an outer circumferential surface 12b of the barrel 12 (the body portion 18). Specifically, the stepped structure 40H includes a protrusion 60 protruding radially outward from the outer circumferential surface 12b of the barrel 12. The protrusion 60 is formed in an annular shape extending in the entire circumference in the circumferential direction. A plurality of the protrusions 60 may be formed at intervals in the circumferential direction.

A range of a step height d6 (a protruding height of the protrusion 60) of the stepped structure 40H is the same as the range of the step height d1 (see FIG. 3) of the stepped structure 40A. As a result, good visibility of the scale 38 can be obtained, and the stepped structure 40H is prevented from being an obstacle in a manufacturing process (for example, interfering conveyance of the barrel 12 by a feeder or the like). A range of an axial width W6 of the protrusion 60 may be the same as the range of the axial width W1 (see FIG. 3) of the protrusion 42 described above. Embossment may be formed on an outer surface 61 of the protrusion 60 in order to make the scale 38 easily visible.

Figure 10B:
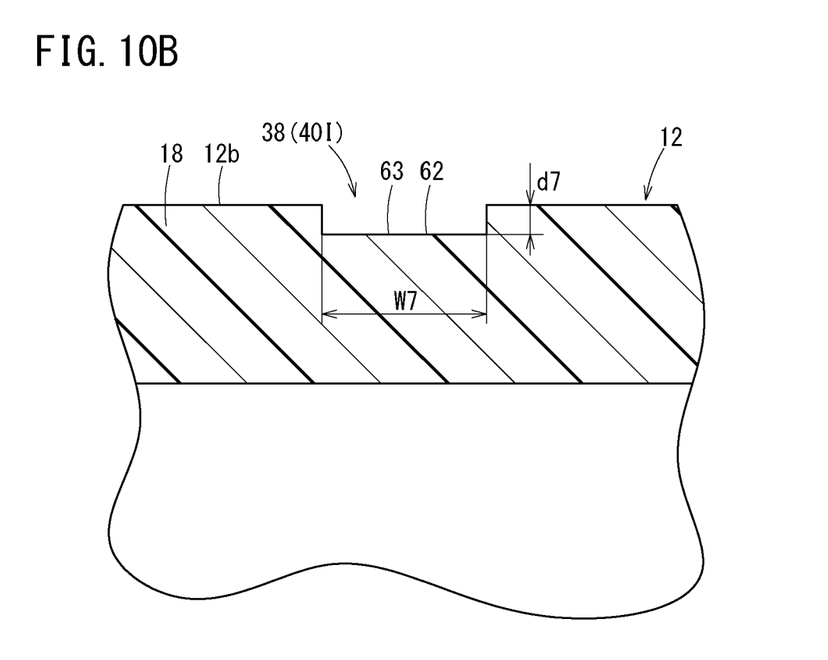
FIG. 10B is an enlarged cross-sectional view of a main part of a syringe barrel having a stepped structure according to a ninth configuration example.

A stepped structure 40I forming the scale 38 illustrated in FIG. 10B has a groove 62 recessed radially inward from the outer circumferential surface 12b of the barrel 12. The groove 62 is formed in an annular shape extending in the entire circumference in the circumferential direction. A plurality of the grooves 62 may be formed at intervals in the circumferential direction. A range of a step height d7 (a depth of the groove 62) of the stepped structure 40I is the same as the range of the step height d2 (see FIG. 4) of the stepped structure 40B. As a result, good visibility of the scale 38 can be obtained, and the stepped structure 40I is prevented from being an obstacle in the manufacturing process. A range of an axial width W7 of the groove 62 may be the same as the range of the axial width W1 (see FIG. 3) of the protrusion 42 described above. Embossment may be formed on an inner surface 63 of the groove 62 (a surface forming the bottom portion of the groove 62) in order to make the scale 38 easily visible.

Figure 11:
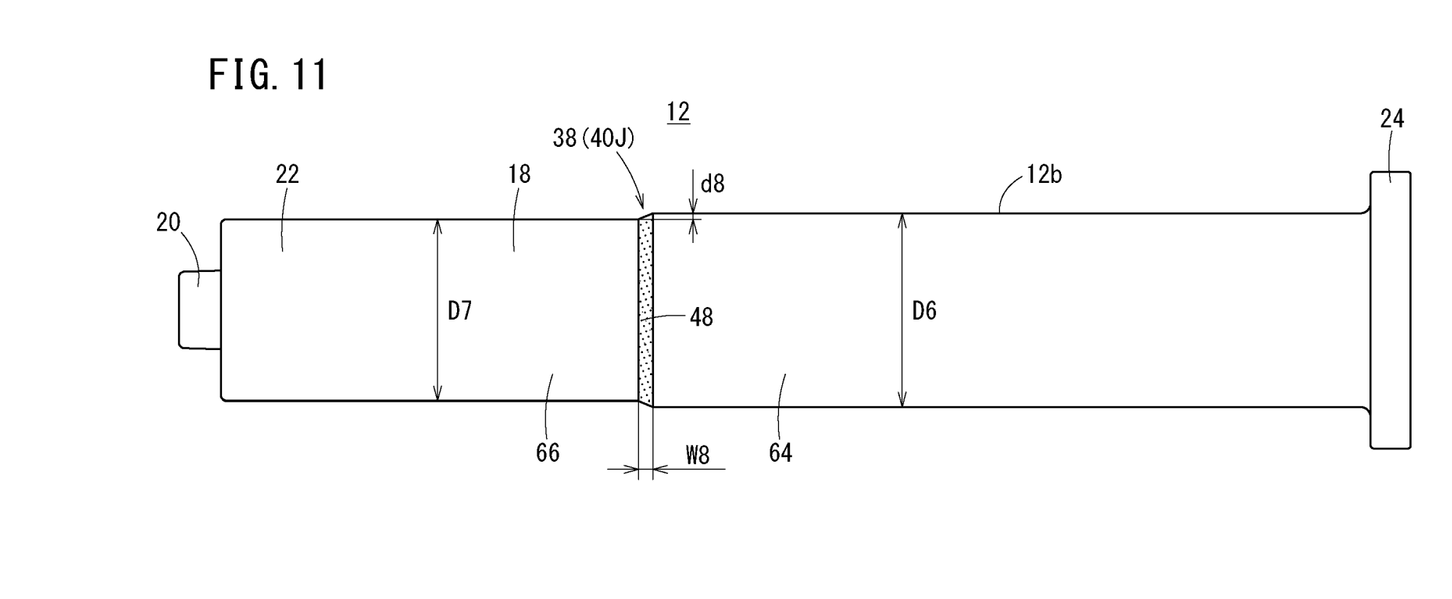
FIG. 11 is an external view of a syringe barrel having a stepped structure according to a tenth configuration example.

A stepped structure 40J forming the scale 38 illustrated in FIG. 11 is formed using an outer diameter difference of the outer circumferential surface 12b of the barrel 12 (the body portion 18). Specifically, the outer circumferential surface 12b of the barrel 12 has a large-diameter portion 64 extending in the axial direction and a small-diameter portion 66 extending in the axial direction and having a smaller inner diameter than the large-diameter portion 64, and the stepped structure 40J is formed using an outer diameter difference between the large-diameter portion 64 and the small-diameter portion 66. The small-diameter portion 66 is formed to be closer to the distal end side than the large-diameter portion 64.

A step height d8 of the stepped structure 40J is a half of a difference between an outer diameter D6 of the large-diameter portion 64 and an outer diameter D7 of the small-diameter portion 66. A range of the step height d8 of the stepped structure 40J is the same as the range of the step height d1 (see FIG. 3) of the stepped structure 40A described above.

In FIG. 11, the embossment 48 is formed on an outer circumferential surface of a distal end portion of the large-diameter portion 64. The embossment 48 is formed in an annular shape extending around the entire circumference in the circumferential direction. A range of an axial width W8 of the embossment 48 may be the same as the range of the axial width W1 (see FIG. 3) of the protrusion 42 described above. In this manner, the stepped structure 40J functioning as the scale 38 can be easily constructed by providing the outer diameter difference on the outer circumferential surface 12b of the barrel 12 and adding the embossment 48.

In addition, the outer circumferential surface of the distal end portion of the large-diameter portion 64 is formed in a tapered shape decreasing in diameter in the distal end direction, and the embossment 48 is formed on such a tapered outer circumferential surface. With this configuration, when the barrel 12 is formed by injection-molding, it is unnecessary to split an outer mold for injection-molding into split molds in order to provide the stepped structure 40J. Thus, it is possible to suppress complication of a metal mold structure accompanying provision of the stepped structure 40J.

Incidentally, the outer circumferential surface of the distal end portion of the large-diameter portion 64 may be formed in a straight shape having an outer diameter that is substantially constant in the axial direction in the barrel 12 illustrated in FIG. 11. In this case, it is preferable that the embossment 48 be formed on the outer circumferential surface of the distal end portion of the large-diameter portion 64 or an outer circumferential surface of a proximal end portion of the small-diameter portion 66.

The application of the barrel 12 provided with the scale 38 is not limited to the prefilled syringe 10, but may be applied to an injector that is filled with the drug solution M after provision of a product.

The present invention is not limited to the above-described embodiments, and various modifications can be made within a scope that does not depart from a gist of the present invention.

What is claimed is:

1. A syringe barrel comprising:
a hollow body portion that is configured such that a gasket is slidably insertable therein;
wherein the syringe barrel is made of a resin that has a total light transmittance of 80% or more;
wherein a stepped structure is disposed at an inner circumferential surface or an outer circumferential surface of the body portion, the stepped structure being visible from an outside of the syringe barrel;
wherein the stepped structure is located at only one position in an axial direction of the body portion so as to allow for adjustment of an amount of a liquid in the syringe barrel to a predetermined dose by advancing the gasket to the stepped structure before administration of the liquid to a patient;
wherein the stepped structure has a step height in a range of 0.001 to 0.15 mm in a radial direction; and
wherein the stepped structure has a width in a range of 0.1 to 0.5 mm in the axial direction.

2. The syringe barrel according to claim 1, wherein the stepped structure is disposed at the inner circumferential surface of the body portion.

3. The syringe barrel according to claim 1, wherein the stepped structure has an annular shape that extends in a circumferential direction of the body portion.

4. The syringe barrel according to claim 1, wherein the stepped structure includes a plurality of stepped structure portions located at intervals in a circumferential direction of the body portion.

5. The syringe barrel according to claim 4, wherein:
the plurality of stepped structure portions located at the intervals in the circumferential direction of the body portion are a plurality of protrusions that protrude radially from the inner circumferential surface of the body portion; and
a plurality of embossments are formed on inner surfaces of the plurality of protrusions.

6. The syringe barrel according to claim 4, wherein:
the plurality of stepped structure portions located at the intervals in the circumferential direction of the body portion are a plurality of grooves that are recessed radially with respect to the inner circumferential surface; and
a plurality of embossments are formed on inner surfaces of the plurality of grooves.

7. The syringe barrel according to claim 1, wherein the stepped structure comprises a protrusion that protrudes radially from the inner circumferential surface or the outer circumferential surface of the body portion.

8. The syringe barrel according to claim 1, wherein the stepped structure comprises a groove that is recessed radially with respect to the inner circumferential surface or the outer circumferential surface of the body portion.

9. The syringe barrel according to claim 1, wherein:
the inner circumferential surface or the outer circumferential surface comprises:
a large-diameter portion extending in the axial direction, and
a small-diameter portion extending in the axial direction and having a smaller diameter than that of the large-diameter portion; and
the stepped structure is located at a transition between the large-diameter portion and the small-diameter portion.

10. The syringe barrel according to claim 9, wherein:
the stepped structure has a roughened surface at the transition between the large-diameter portion and the small-diameter portion.

11. The syringe barrel according to claim 9, wherein the stepped structure has a roughened surface.

12. The syringe barrel according to claim 1, wherein:
the stepped structure comprises a protrusion that protrudes radially from the inner circumferential surface of the body portion; and
an embossment is formed on an inner circumferential surface of the protrusion.

13. A prefilled syringe comprising:
the syringe barrel according to claim 1;
the gasket, which is slidably inserted inside the syringe barrel;
a plunger that is configured to press the gasket in a distal end direction; and
the liquid filled in a liquid chamber formed by the syringe barrel and the gasket.

14. The syringe barrel according to claim 1, wherein the step height of the stepped structure is in a range of 0.01 to 0.1 mm in the radial direction.

15. The syringe barrel according to claim 1, wherein the step height of the stepped structure is in a range of 0.01 to 0.03 mm in the radial direction.

* * * * *